United States Patent

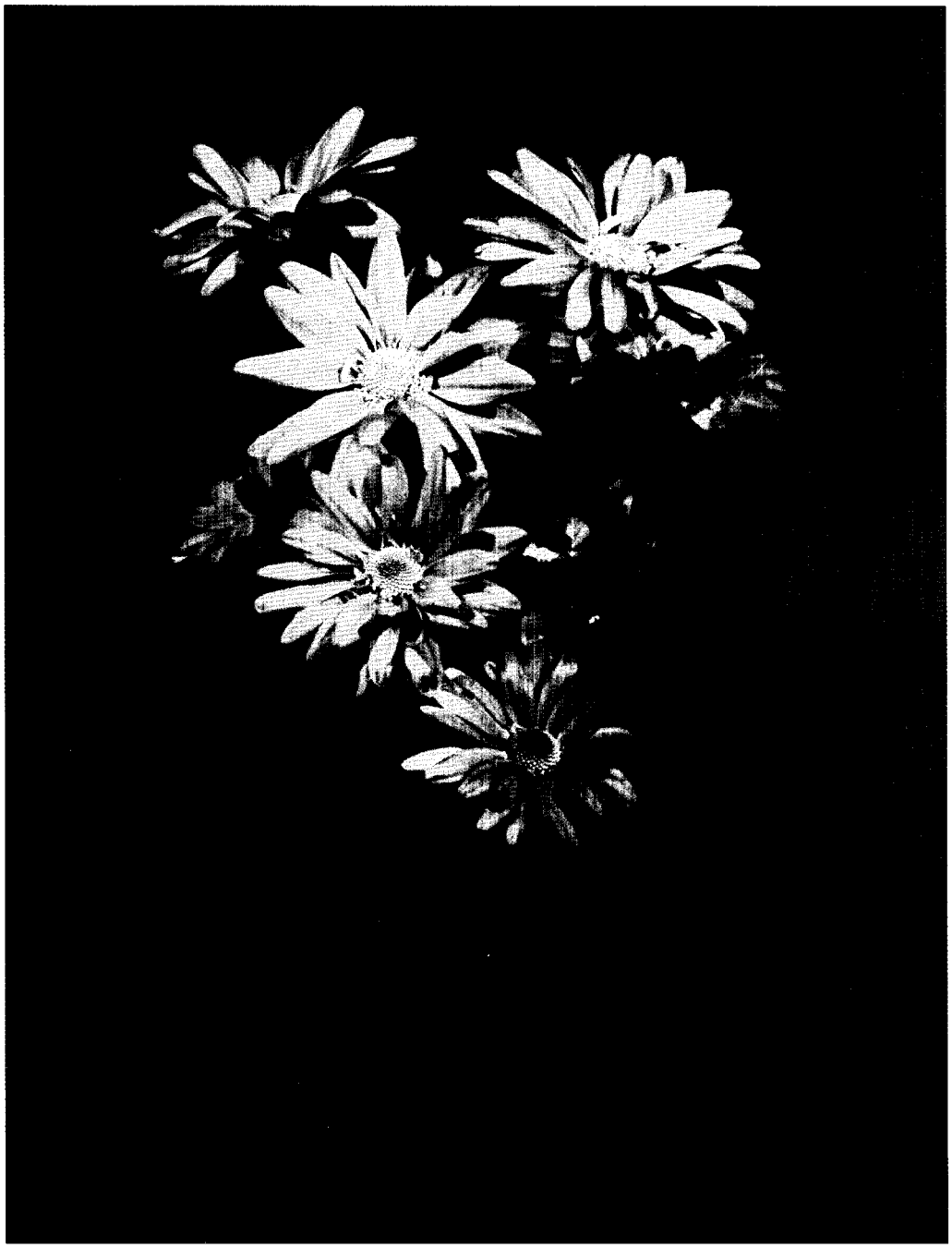

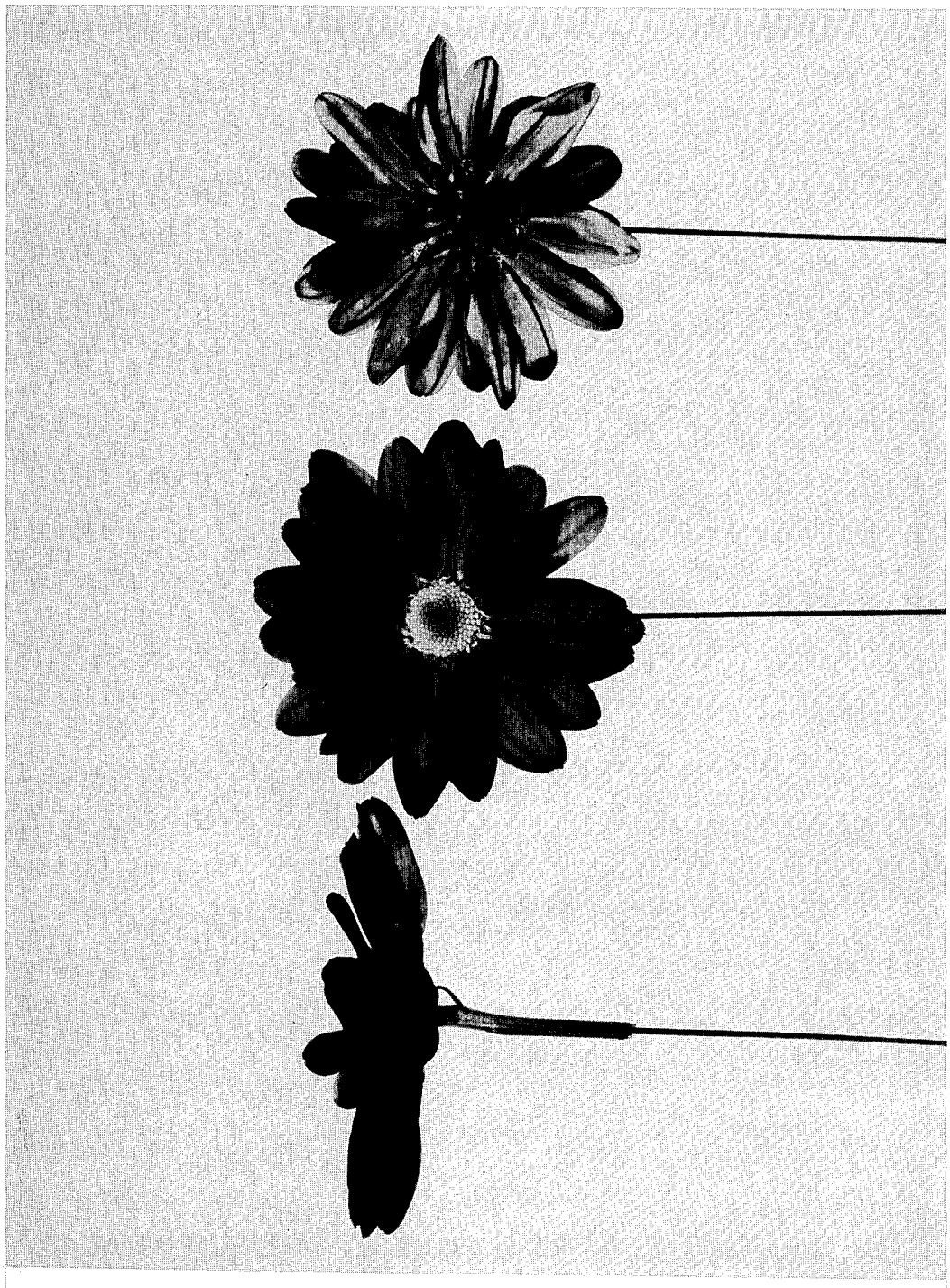

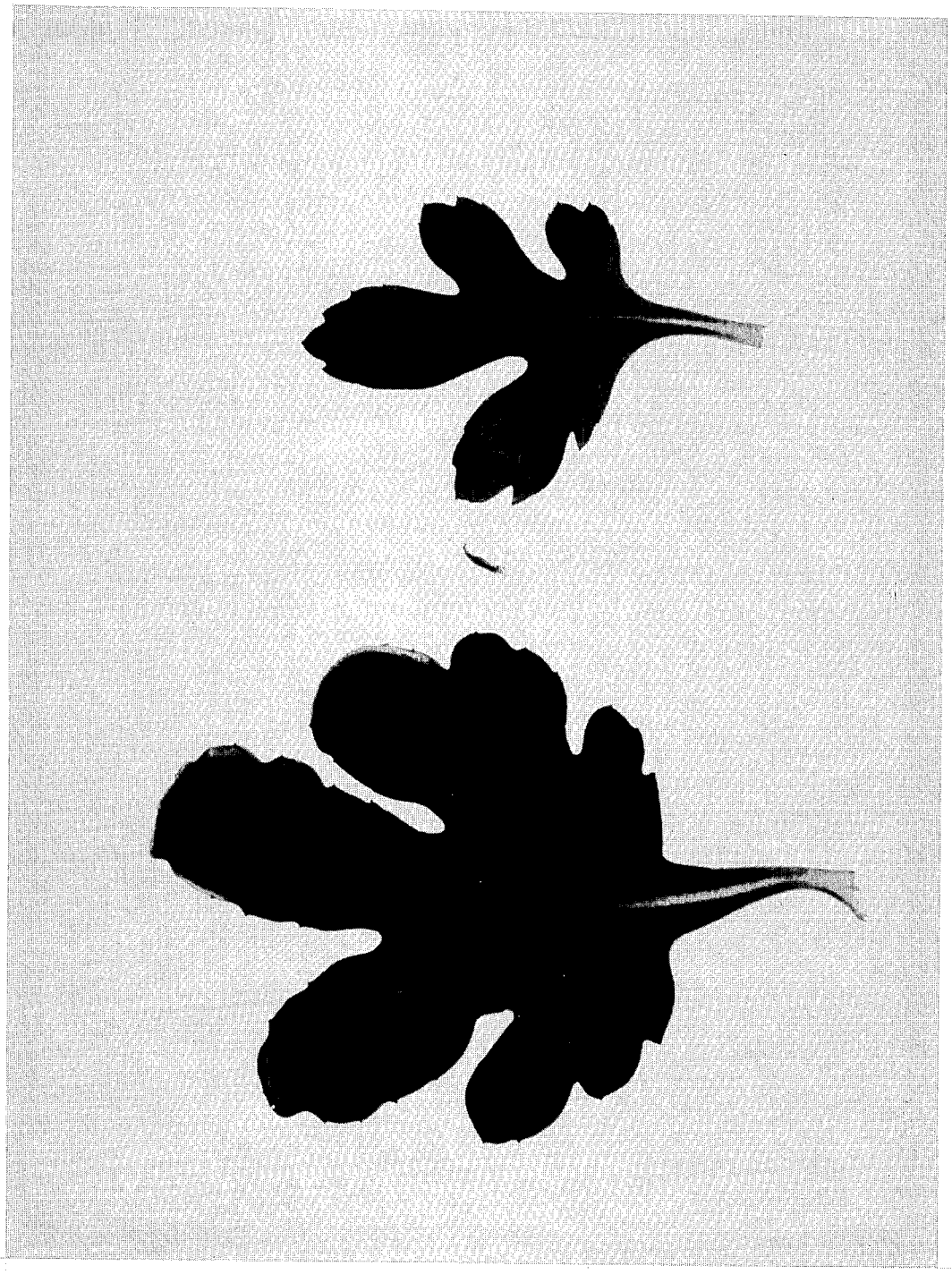

Plant Pat. 3,945
Patented Aug. 24, 1976

3,945

CHRYSANTHEMUM PLANT

Walter H. Jessel, Jr., Doylestown, and William E. Duffett, Akron, Ohio, assignors to Yoder Brothers, Inc., Barberton, Ohio

Filed July 16, 1975, Ser. No. 596,101
**Int. Cl.[2] A01H *5/00***
U.S. Cl. Plt.—74 1 Claim

The present invention comprises a new and distinct cultivar of *Chrysanthemum morifolium, Ramat.*, hereinafter referred to by the cultivar name Accent (#72117011).

Accent was originated from a cross made in a controlled breeding program in Barberton, Ohio in the year 1971. The female, or seed parent, was Dramatic (#67079001; U.S. Plant Pat. #3,189), a bronze daisy originated by the present inventors from a cross between Dazzler (#65093001; unpatented; commercially available) and #65013002 (unnamed seedling). The male, or pollen parent of Accent, was Melody (#63001005; unpatented; commercially available), a lavender pink daisy originated by the present inventors from a cross between #22005E03 (unnamed seedling) and #60137002 (unnamed seedling). Dazzler, #65013002, #22005E03, and #60137002 were all products of the breeding program of the present inventors.

Accent is a product of a planned breeding program which had the objective of creating cultivars for use as cut sprays with daisy inflorescence type, intense lavender and purple inflorescence color, and with resistance to color oxidation or anthocyanin breakdown under the stress of high temperatures. Such traits were not present in combination in previously available commercial cultivars.

Accent was discovered and selected as a flowering plant within the progeny of the stated cross by William E. Duffett and Walter H. Jessel, Jr. on Oct. 31, 1972 in a controlled environment in Barberton, Ohio.

The first act of asexual reproduction of Accent was accomplished when vegetative cuttings were taken from the initial selection in March 1973 in a controlled environment in Barberton, Ohio by a technician working under formulations established and supervised by William E. Duffett and Walter H. Jessel, Jr. Horticultural examination of selected units initiated May 3, 1973 has demonstrated that the combination of characteristics as herein disclosed for Accent are firmly fixed and are retained through successive generations of asexual reproduction.

Accent has not been observed under all possible environmental conditions. The phenotype may vary significantly with variations in environment such as temperature, light intensity, and daylength. The following observations, measurements, and comparisons describe plants grown in Barberton, Ohio under greenhouse environmental conditions which approximate those generally used in commercial practice, as described in Chart A and Chart B which appear at the end of the present specification.

The following traits have been repeatedly observed and are determined to be basic characteristics of Accent which in combination distinguish this chrysanthemum as a new and distinct cultivar:

(1) Flat inflorescence form, not known to reflex.
(2) Daisy inflorescence type.
(3) Purple ray floret color with minimal color oxidation.
(4) Medium green disc floret color at immature, unopened stage.
(5) Minimal pollen development.
(6) Diameter across face of inflorescence ranging from 3.0 to 4.0 inches at maturity.
(7) Uniform nine week flowering response period.
(8) Medium plant height.
(9) Semi-upright branching pattern.

The accompanying photographic drawings show typical inflorescence and foliage characteristics of Accent with colors being as nearly true as possible with illustrations of this type. Sheet 1 is a color photograph of Accent. Sheet 2 is a black and white photograph showing three views of the inflorescence of Accent. Sheet 3 is a black and white photograph showing the foliage of Accent at three stages of growth.

Among currently available commercial cultivars which are well known to the present inventors, Accent most closely compares to the paternal cultivar, Melody. Reference is made to attached Chart C which compares certain characteristics of Accent with the same characteristics of Melody. General comparisons are as follows:

(1) In comparison to Melody, Accent has more intense purple ray floret color, shorter plant height, later flowering response period, and smaller diameter across face of inflorescence. The general branching pattern, and inflorescence form and type of Accent are similar to those of Melody.

In the following description, color references are made to The Munsell Limit Color Cascade, 1972 edition. The color values were determined between 4:00 and 4:30 p.m. on Mar. 24, 1975 under 160 foot-candle light intensity at Barberton, Ohio.

BOTANICAL CLASSIFICATION

*Chrysanthemum morifolium*, Ramat., cv Accent.

I. Inflorescence

A. Capitulum:
*Form.*—Flat.
*Type.*—Daisy.
*Permanence.*—14–20 days.
*Diameter across face.*—3.0 to 4.0 inches.

B. Corolla of ray florets:
*Texture (adaxial).*—Glabrous.
*Appearance and form.*—Ligulate.
*Arrangement.*—Whorled on receptacle.
*Persistence.*—Resists shatter.

*Color* (*abaxial*).—Approximately 43–13 to 45–5 overlaid with 44–9.

*Veination.*—Prominent.
*Margin.*—Slightly serrated.

CHART A—AVERAGE GREENHOUSE CHRYSANTHEMUM ENVIRONMENTS USED FOR BARBERTON, OHIO

| Season | Temperatures used (°F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m.; off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m.; off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

*Color* (*adaxial*).—Approximately 45–4 to 43–12 over white.

C. Corolla of disc florets:

*Appearance and form.* — Gamopetalous; tubular; 5 lobed.

*Color.*—22–11 to 25–8.

D. Reproductive organs:

*Androecium.*—Present disc florets only; syngenesious stamen; scant pollen.

*Gynoecium.*—Present both ray and disc florets; inferior, bicarpellate ovary; single style; 2-lobed stigma.

II. Plant

A. General appearance: Semi-upright; medium height.

B. Duration and texture: Perennial; herbaceous.

C. Foliage.

*Color* (abaxial).—Approximately 21–13 to 21–15 but with more grey.

*Color* (*adaxial*).—Approximately 21–13 but duller and with more grey.

*Shape.*—Spatulate; deeply lobed.

*Texture.*—Glabrous.

*Arrangement.*—Alternate.

CHART B

INTENSITY OF DIRECT SOLAR RADIATION

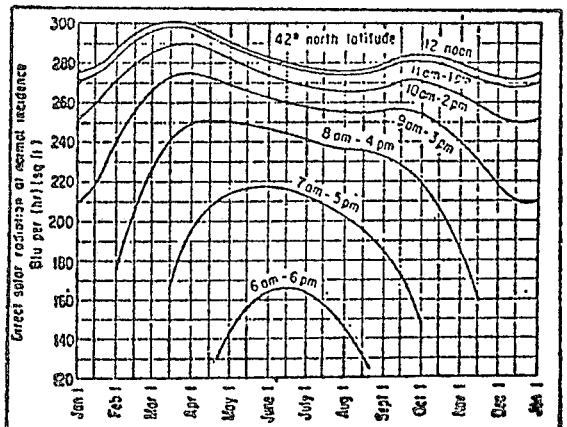

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF ACCENT AND MELODY

| Cultivar | Inflorescence color | Plant height | Flowering response period (week) | Branching pattern | Diameter across face of inflorescence (inches) | Inflorescence form and type |
|---|---|---|---|---|---|---|
| Accent | Purple | Medium | 9 | Semiupright | 3.0 to 4.0 | Flat daisy. |
| Melody | Lavendar pink | Very tall | 8 | do | 2.75 to 3.75 | Do. |

NOTE.—Comparisons made of plants grown in a greenhouse in Barberton, Ohio, under conditions as described in Chart A and Chart B.

We claim:

1. A new and distinct cultivar of chrysanthemum known by the cultivar name Accent and particularly characterized as to uniqueness by the combined features of flat inflorescence form, not known to reflex; daisy inflorescence type; purple ray floret color with minimal color oxidation; medium green disc floret color at immature, unopened stage; minimal pollen development; diameter across face of inflorescence ranging from 3.0 to 4.0 inches at maturity; uniform nine week flowering response period; medium plant height, and semi-upright branching pattern.

No references cited.

ROBERT E. BAGWILL, Primary Examiner